US006416735B1

(12) United States Patent
Carroll et al.

(10) Patent No.: US 6,416,735 B1
(45) Date of Patent: Jul. 9, 2002

(54) LIGANDS FOR α-7 NICOTINIC ACETYLCHOLINE RECEPTORS BASED ON METHYLLCACONITINE

(75) Inventors: Frank Ivy Carroll, Durham; Hernán A. Navarro, Chapel Hill; Philip Abraham, Cary; Desong Zhong, Apex, all of NC (US)

(73) Assignee: Research Triangle Institute, Research Triangle Park, NC (US)

( * ) Notice: Subject to any disclaimer, the term of this patent is extended or adjusted under 35 U.S.C. 154(b) by 0 days.

(21) Appl. No.: 09/435,614

(22) Filed: Nov. 8, 1999

(51) Int. Cl.$^7$ ................................................. A61K 51/00
(52) U.S. Cl. ..................... 424/1.81; 424/1.85; 424/1.89
(58) Field of Search ............................... 424/1.85, 1.81, 424/1.89; 546/39; 540/466; 548/404

(56) References Cited

U.S. PATENT DOCUMENTS

| | | | |
|---|---|---|---|
| 5,725,838 A | * 3/1998 | Pollak et al. ............... | 424/1.85 |
| 5,726,189 A |   3/1998 | London et al. ............. | 514/339 |
| 5,750,089 A | * 5/1998 | Neumeyer et al. ......... | 424/1.85 |

OTHER PUBLICATIONS

Davies, Andrew R.L. et al., Characterization of the binding of [3H]methyllycaconitine, Neuropharmacology 38 (5), pp. 679–690, 1999.*

Ward, et al; "Methyllyacaconitine: a selective probe for neuronal α–bungarotoxin binding sites"; *FEBS Letters*; Sep. 1990; vol. 270, No. 1, 2, pp. 45–48.

*Chemical Abstracts*: vol. 96, No. 13, Mar. 29, 1982 (Columbus Ohio, USA), p. 154, col. 2, the Abstract No. 98230e, Prinz, et al.; Interaction of Ifuorescent analogs of aetylcholine with nicotinic acetylcholine receptors and acetylcholine esterase; Drug Recept. Their Eff., [Rep. Symp.] 1980 (Pub. 1981), 87–95 (Eng).

Jacyno, et al.; "Synthetic and pharmacological studies on the neurotoxic Delphinium alkaloid methyllycaconitine and related compounds"; Current Topics in Plant Physiology. An American Society of Plant Physiologists Series. *Phytochemicals and Health*; Tenth Annual Penn State Symposium in Plant Physiology; 18–20, May 1995, vol. 15, pp. 294–296.

* cited by examiner

*Primary Examiner*—Michael G. Hartley
(74) *Attorney, Agent, or Firm*—Oblon, Spivak, McClelland, Maier & Neustadt, P.C.

(57) ABSTRACT

Ligands for nAChRs are provided based on various derivatives of methyllycaconitine (MLA) such as radiolabeled MLA, and MLA containing a fluorimetric marker group and their use in imaging for detection of Alzheimer's and other CNS diseases, and combinatorial assays for detection of compounds having affinity for nAChRs, as well as injectable compositions containing the same and kits for performing the imaging studies.

13 Claims, No Drawings

LIGANDS FOR α-7 NICOTINIC ACETYLCHOLINE RECEPTORS BASED ON METHYLLCACONITINE

BACKGROUND OF THE INVENTION

1. Field of the Invention

The present invention relates to new ligands for nicotinic acetylcholine receptors (nAChRs), particularly radioligands and fluorimetric ligands based on methyllycaconitine (MLA).

2. Discussion of the Background

Neuronal nicotine acetylcholine receptors (nAChRs) represent a major neurotransmitter receptor superfamily responsible for excitatory neurotransmission (Lindstrom et al. *Ann. N. Y. acad Sci.*, 1995, 757, 100–116). The α4βn and α7 nAChR are the major receptors in the human brain. These receptors are of great interest since they appear to play a critical role in tobacco dependence and neurodegenerative disease. In particular, the nAChRs have been targeted for the development of drugs for cognitive function, Parkinson's disease, analgesia, inflammatory bowel disorder, schizophrenia, anxiety, depression, Tourette's syndrome and smoking cessation. For example, the addictive nature of cigarette smoking can be attributed to the reinforcing properties of nicotine (Corrigall et al. *Psychopharmacology*, 1992, 107, 285–289), and nicotine, which binds to nAChRs with high affinity, has been utilized in various smoking cessation therapeutics (Balfour et al. *Pharmacol. Ther.*, 1996, 72, 51–81). In post-mortem autoradiographic studies on Alzheimer's disease tissue, several groups have consistently revealed significant reduction of nAChRs in comparison to controls (Whitehouse et al. *Brain Res.*, 1986, 371, 146–151; Nordberg et al. *Neurosci. Lett.* 1986, 72, 115–119; London et al. *Neurochem. Res.*, 1989, 14, 745–750). In addition, nicotine appears to improve cognitive functions (Lippielo *Alzheimer's Disease. Therapeutic Strategies*, 1994, E. Giacobini and R. Bekcer, Ed., Boston, Birkhauser, 186–190). These results have prompted the pharmaceutical industry to explore the development of safe and effective nAChR-based therapeutic agents for treatment of Alzheimer's disease (Brioni et al. *Adv. Pharmacol.*, 1997, 37, 153–214).

Over the past few years considerable effort has been directed toward the identification and characterization of radioligands for nicotinic acetylcholine receptors (nAChRs) (Holladay et al, *J. Med. Chem.* 1997, 40, 4169–4194). Two major classes of nicotinic receptors have been identified in rat and human brain based on whether they demonstrate high affinity binding for either [$^3$H]nicotine or [$^{125}$I]α-bungarotoxin ([$^{125}$I]α-BGT) (Marks et al, *Mol. Pharmacol.* 1982, 22, 554–564. Heteromeric receptors composed of α and β subunits bind [$^3$H]nicotine with high affinity. The α4β2 receptor is the most common subtype comprising almost 90% of rat brain nAChRs (Lindstrom et al, *Ciba Found Symp.* 1990, 152, 23–52). Receptors with high affinity for [$^{125}$I]a-BGT contain only the α7 subunit (Clarke et al, *J. Neurosci.* 1985, 5, 1307–1315; Seguela et al, *J. Neurosci.* 1993, 13, 596–604) and display a regional distribution distinct from the αβ heteromeric receptors (Marks et al, *Mol. Pharmacol.* 1982, 22, 554–564; Marks et al, *Mol. Pharmacol.* 1986, 30, 427–436). Several new tritium and iodine-125 ligands have been developed for studying the pharmacological properties of α4β2 nAChRs (Houghtling et al, *Mol. Pharmacol.* 1995, 48, 280–287; Davila-Garcia et al, *J. Pharmacol Exp. Ther.* 1997, 282, 445–45 1; Horti et al, *Nucl. Med. Biol.* 1999, 26, 175–182; Musachio et al, *Synapse* 1997, 26, 392–399; Musachio et al, *Life Sci.* 1998, 62, PL 351–357; Scheffel et al, *NeuroReport* 1995, 6, 2483–2488.). In addition, several carbon-11, fluorine-18, and iodine-123 positron emission tomography (PET) and single-photon emission computed tomography (SPECT) tracers have been developed for in vivo imaging of α4β2 nAChRs (Horti et al, *Nucl. Med. Biol.* 1999, 26, 175–182; Musachio et al, *Synapse* 1997, 26,392–399; Musachio et al, *Life Sci.* 1998, 62, PL 351–357; Ding et al, *Synapse* 1996, 24, 403–407; Ding et al, Mapping nicotinic acetylcholine receptors with PET, Society for Neuroscience, Washington, D.C., 1996, Abstract 22, 269; Horti et al, *J. Labelled Compd. Radiopharm.* 1996, 38, 355–365; Ding et al, *Nucl. Med. Biol.* 1999, 26, 139–148; Gatley et al, *Nucl. Med. Biol.* 1998, 25, 449–454; Ding et al, *J. Label Compds. Radiopharm.* 1997, 39, 827–832; Liang et al, *J. Med. Chem.* 1997, 40, 2293–2295; Loc'h et al, *J. Labelled Compd. Radiopharm.* 1997, 40, 519–521; Patt et al, *Nucl. Med. Biol.* 1999, 26, 165–173; Dolle et al, *J. Med. Chem.* 1999, 42, 2251–2259; Dolci et al, *Bioorg. Med. Chem.* 1999, 7, 467–479; Horti et al, *J. Labelled Comp. Radiopharm.* 1998, 41, 309–318; Horti et al, *J. Med. Chem.* 1998, 41, 4199–4206; Horti et al, *Nucl. Med. Biol.* 1998, 25, 599–603). At present, [$^{125}$I]-α-BGT is the only iodine-labeled radioligand specific for the α7 nAChR. α-BGT is a 7800–8000 kD 74 amino acid polypeptide isolated from snake venom, *Bungarus multicinctus* (Mebs et al, *Became. Biophys. Res. Commun.* 1971, 44, 711–716.) The radioligand has the disadvantage of big nonspecific binding in filtration-based assays. Moreover, α-BGT does not cross the blood-brain barrier limiting its use for imaging studies for the α7 nAChR.

Neuronal [$^{125}$I]α-BGT binding sites, a subtype of nicotinic receptors, are altered in a number of CNS disorders such as schizophrenia and Parkinson's disease (Freedman et al. *Proc. Natl. Acad. Sci. USA,* 1997, 94, 587–592). A good correlation has been noted between the distribution of α7 mRNA subunits and that of the high affinity binding sites for α-BGT in rodent brain (Clarke et al. *J. Neurosci.*, 1985, 5, 1307–1315; Seguela et al. *J. Neurosci.*, 1993, 13, 596–604). However, potent and selective agonists and antagonists at the α7 nicotinic receptor subtype are lacking. Methyllycaconitine (MLA), a natural product isolated from the seeds of *Delphinium brownii,* has high affinity to neuronal [$^{125}$I]α-BGT binding sites ($K_i$=4 nM), in contrast to its much weaker interactions with the α-bungarotoxin-sensitive nicotinic receptor subtype present on the neuromuscular junction and with other nicotinic receptor subtypes labeled by [$^3$H] nicotine. MLA blocked the activation of α7 receptor subtype expressed in oocytes with an $IC_{50}$ in the picomolar range (Palma et al. *J. Physiol.*, 1996, 491, 151–161). The selectivity of MLA towards the brain α-bungarotoxin-sensitive receptor subtype, i.e. α7, makes this agent very useful for studying the properties of this subtype in vitro. In contrast to α-BGT, MLA is a relatively small reversible binding compound. In addition, Turek et al (Turek et al. *J. Neurosci. Meth.* 1995. 61, 113–118) showed that peripherally administered MLA crosses the blood-brain barrier and may, therefore, be a useful tool to further probe the CNS functions of the α7 nicotinic receptor subunit in vivo.

In general, imaging drug and neurotransmitter receptors by PET or SPECT is very useful. For example, dopamine transporters can be imaged, and this procedure shows great promise as a diagnostic approach for Parkinson's disease (Kuhar et al. *Neurotransmitter Transporters: Structure and Function,* 1997, M. E. A. Reith, Ed., Totowa, N.J., Human Press, Publishers, 297–313; Innis et al. *Proc. Natl. Acad Sci. USA,* 1993, 90, 11965–11969; Frost et al. *Ann. Neurol.,*

1993, 34, 423–431) as a method to determine the doses of therapeutic drugs needed to achieve significant receptor occupancy and, therefore, therapeutic benefit (Scheffel et al. *Synapse*, 1994, 16, 263–268) and as a method to reflect the level of neurotransmitter present in the synapse and the activity of central cholinergic systems (Volkow et al. *Synapse*, 1994, 16, 255–262).

Tomographic imaging studies of central nAChRs in living subjects have been hampered by the absence of radiotracers that possess favorable in vivo properties. Although [C-11] (−)nicotine has been utilized to study nAChRs in humans, its high nonspecific binding and flow-dependent tissue retention make it less than ideal as an in vivo probe (Nyback et al. *Psychopharmacology* (*Berl.*), 1994, 115, 31–36). Research efforts, therefore, have focused on development of new nAChR radioligands including [F-18] and [$^{123}$I]-labeled analogs of the potent nAChR agonist epibatidine. These radiolabeled epibatidine derivatives have successfully imaged α4β2 nAChRs with high specificity in non-human primate (Ding et al. *Synapse*, 1996, 24, 403–407; Musachio et al. *Synapse*, 1997, 26, 392–399; Villemagne et al. *J. Nucl. Med*, 1997, 38, 1737–1741). No iodine-radiolabeled ligands are available for imaging the α7 nAChR.

SUMMARY OF THE INVENTION

Accordingly, one object of the present invention is to provide a new ligand for nAChRs that provides high specificity binding.

A further object of the present invention is to provide radioligands based on MLA.

Another object of the present invention is to provide fluorimetric ligands based on MLA.

Another object of the present invention is to provide an assay for nAChR activity using the ligand of the present invention for detection and quantitation.

These and other objects of the present invention have been satisfied by the discovery of ligands for nAChRs having the structure:

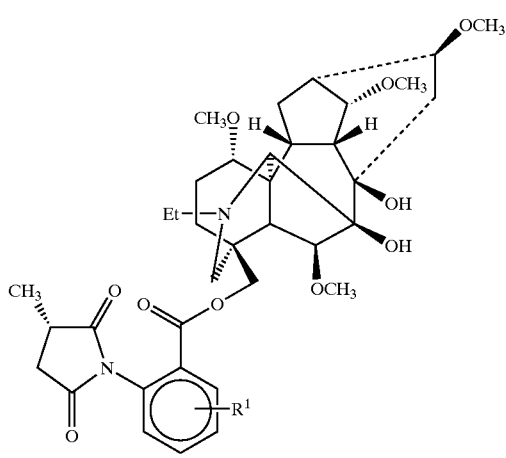

where $R^1$ is a detectable marker group, preferably a radioisotope or a fluorimetric marker group, and its use in imaging and assays for measuring nAChR activity.

DETAILED DESCRIPTION OF THE PREFERRED EMBODIMENTS

The present invention relates to ligands for nAChRs based on methyllycaconitine having the formula (I):

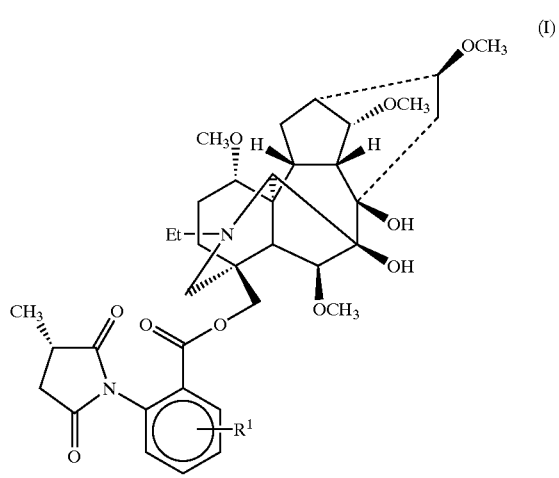

where $R^1$ is a detectable marker group. The detectable marker group can be any group that can be sensitively detected using conventional methods. Preferably, $R^1$ is a radioisotope or a fluorimetric marker group. The present ligands have high specificity for the α7 nAChR sites and provide diagnostic imaging agents for detection of Alzheimer's disease and other CNS disorders and determination of dosing levels for CNS disorders. In addition, the ligands can be used in high throughput assays using rat brain homogenates for detection of α7 nAChR compounds synthesized by combinatorial methods.

The ligand of the present invention is preferably a radioligand, as these can be used in both in vitro assays and in vivo imaging. Suitable radioisotopes for use as $R^1$ include $^{125}$I, $^{123}$I, $^{124}$I, $^{120}$I, $^{11}$C (as part of a $C_1$–$C_4$-alkyl group), and $^{18}$F, with the Iodine radioisotopes being preferred, most preferably $^{125}$I or $^{123}$I. The ability of MLA compounds to cross the blood-brain barrier makes the present ligands particularly useful for in vivo imaging of the living human brain. Most preferably, the present ligand is $^{125}$I-MLA ($R^1=^{125}$I) having the structure [$^{125}$I]iodo-MLA shown in Scheme I. For SPECT imaging studies, the [$^{123}$I]iodo-MLA compound, having the $^{123}$I substitution in the same location as the $^{125}$I, is preferred. This compound is readily prepared by the same method shown in Scheme I, using sodium [$^{123}$I] iodide in place of sodium [$^{125}$I]iodide.

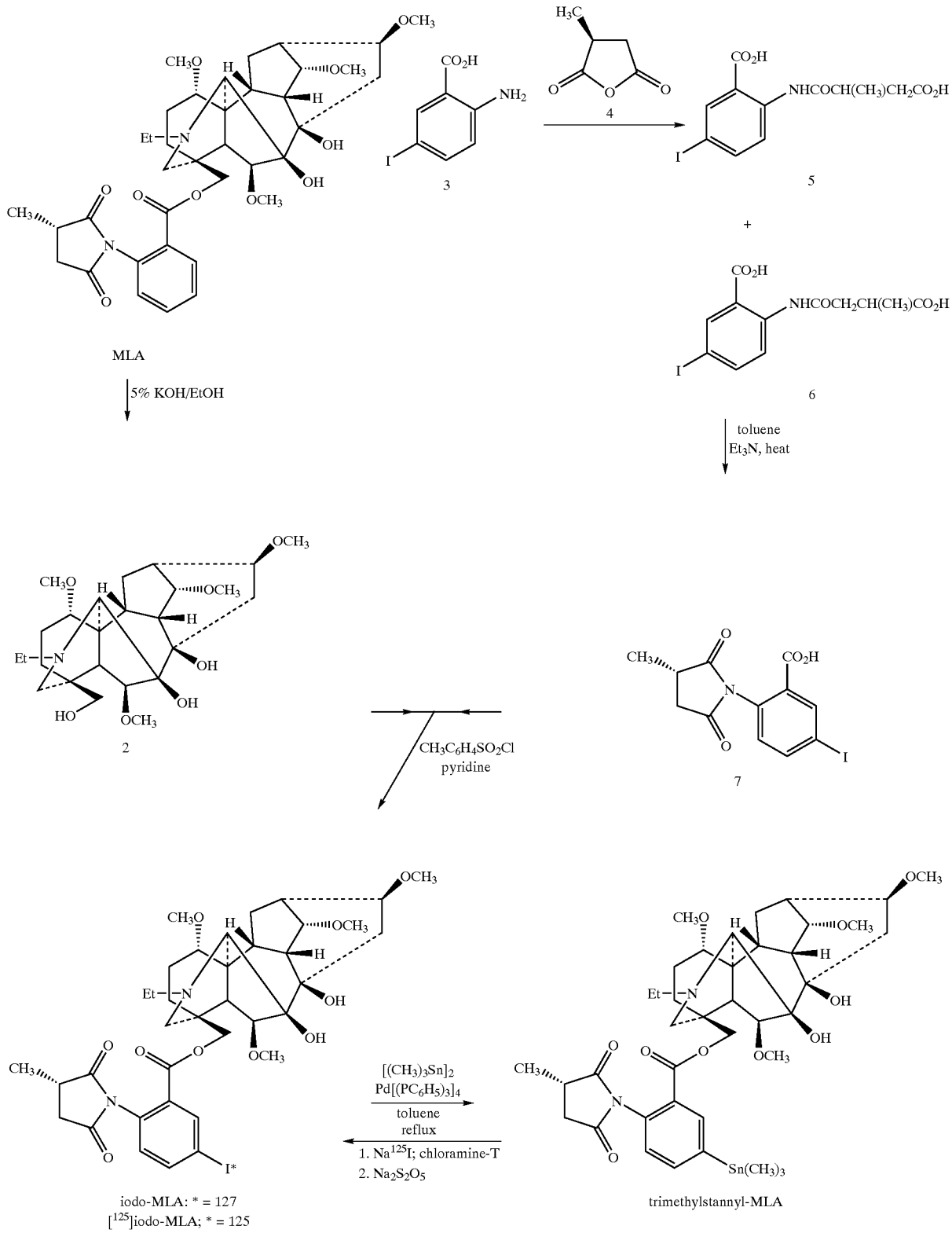
Scheme I
For in vitro assays, such as combinatorial assays, the ligand can use any readily detectable marker group, preferably radioisotopes, or fluorimetric marker groups as $R^1$. Suitable radioisotopes include those noted above. Fluorimetric marker groups must be capable of generating a fluorescent signal, but must not interfere with the binding specificity of the MLA molecule with α7 nAChRs. Suitable fluorimetric marker groups include those having the structures a–m, below.
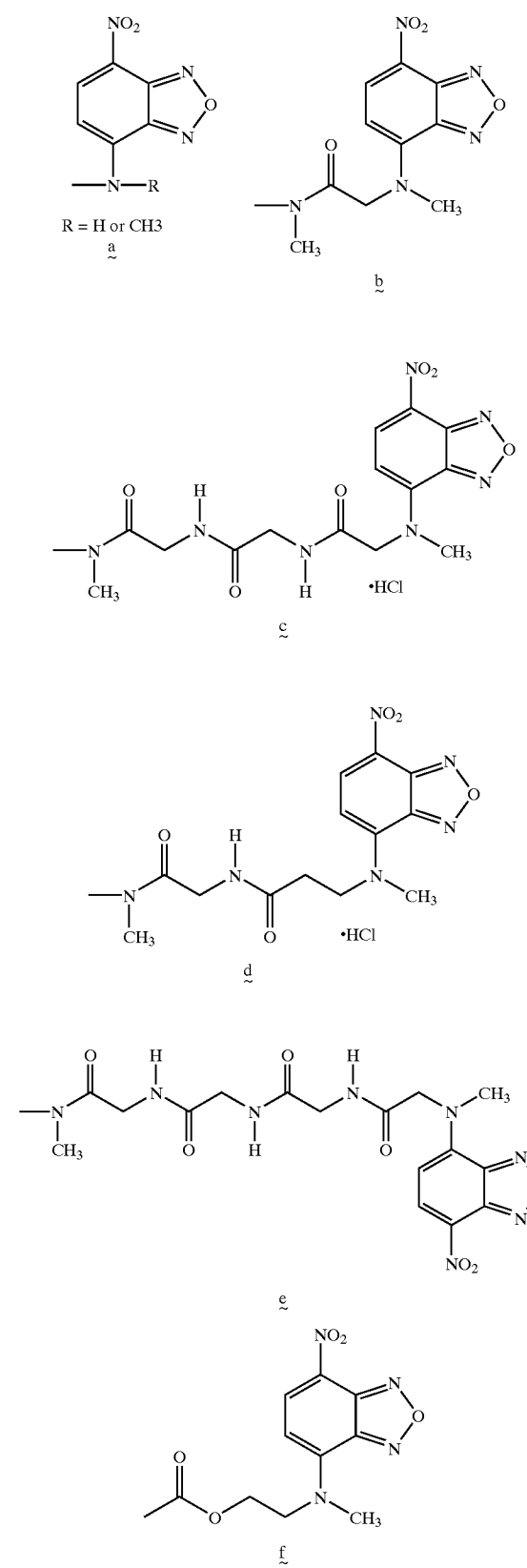
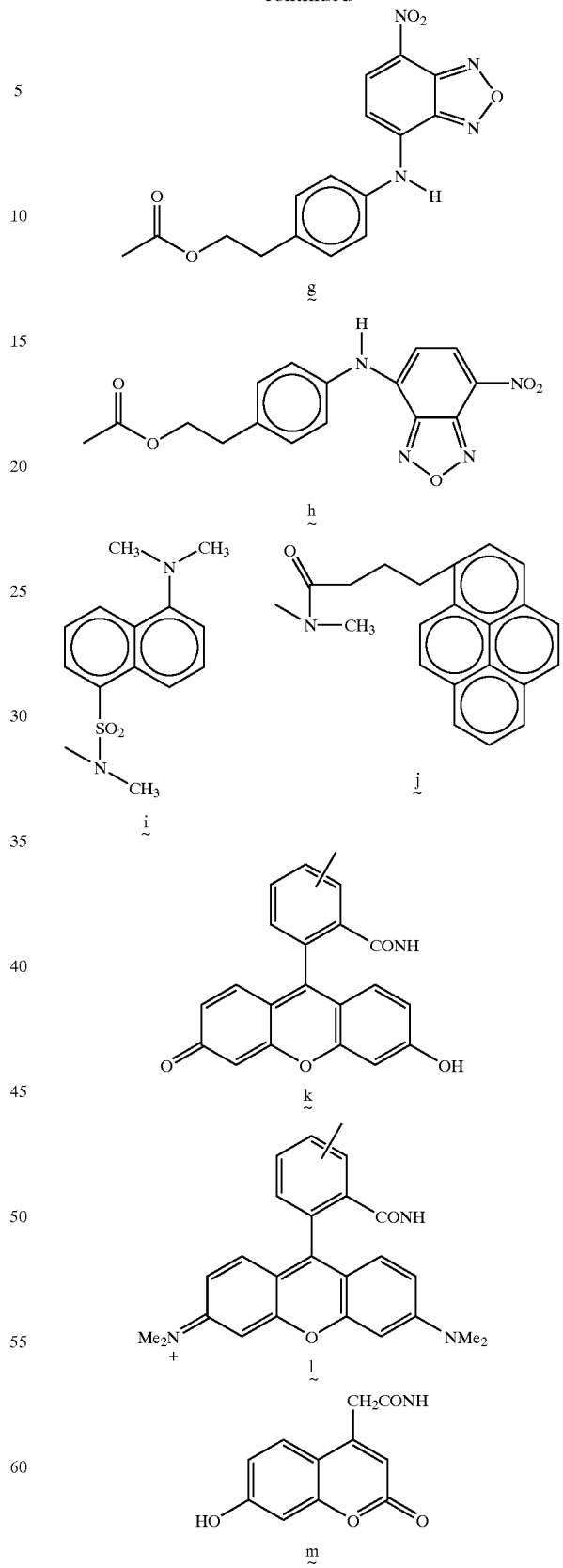
These groups are well known fluorimetric markers that can be provided on the MLA molecule using conventional synthetic techniques, particularly from the I-MLA or trimethylstannyl-MLA compound of Scheme I. Also, the fluorimetric markers can be provided by preparation of the nitro-MLA compound (having —$NO_2$ in place of I), followed by reduction to amino and coupling of the fluorimetric marker group to the MLA structure. The methods for these reactions are well known in the art. Most preferably, the fluorimetric marker group is a group having a structure selected from the group consisting of structures a–h, with the most preferred groups being those with longer linking chains (structures b–h).

The most preferred embodiment, [$^{125}$I] iodomethyllycaconitine ([$^{125}$I]iodo-MLA), can be synthesized by the route outlined in the following Scheme I. MLA is isolated from *Delphinium elatum* (Pacific giant) seeds according to the procedure developed by Pelletier and co-workers (Pelletier et al, *Tetrahedron* 1989, 45, 1887–1892). Alkaline hydrolysis of MLA using 5% potassium hydroxide in ethanol gives the ester-free lycaconitine (2) (Pelletier et al, *J. Nat. Prod.* 1980, 43, 395–406). Treatment of 5-iodoanthranilic acid (3) with (S)-methylsuccinic anhydride (4) provides a mixture of the iodomethyllycaconitinic acids (5 and 6). The $^1$H-NMR spectrum of the acids show two equal doublets at 1.29 and 1.26 ppm (J=7.1 Hz) for the —CH—$CH_3$ groups which suggests that the acids are a 1:1 mixture of 5 and 6. The mixture of acids is refluxed under a Dean Stark tube in toluene containing triethylamine for 24 h to yield (S)-2-(methylsuccinimido)-5-iodobenzoic acid (7). The structure and single isomer nature of 7 is established by the $^1$H NMR spectrum which shows only one doublet at 1.37 ppm (J=6.8 Hz) for the CH—$CH_3$ group. The acid 7 is coupled to the primary alcohol group of lycoctonine in the presence of p-toluenesulfonyl chloride and pyridine to give iodo-MLA. Refluxing iodo-MLA with hexamethyldistannane in toluene in the presence of palladium-tetrakis-triphenylphosphine provides trimethylstannyl-MLA which is the precursor needed to prepare [$^{125}$I]iodo-MLA. This trimethylstannyl-MLA can also be used as the starting material for a variety of reactions to generate the various ligands of the present invention, including radio-ligands and fluorimetric ligands, using conventional chemical reactions well known to those of skill in the art.

The present invention also provides compounds that are precursors to the ligands of the present invention. In particular, these precursors have $R^1$ being a group that is readily converted into the desired detectable marker group. Preferably, $R^1$ in the precursor compounds is tri-hydrocarbyl-silyl or tri-hydrocarbyl-stannyl, preferably the trimethylsilyl and trimethylstannyl compounds. Most prefereably, the precursor compound is a trimethylstannyl-MLA compound. In a typical preparation of a radioligand and use in imaging, the person doing the imaging study will purchase the trimethylstannyl-MLA compound and convert it to the radioligand immediately prior to use, particularly if the radioligand has a relatively short half-life. This avoids degradation of the radioligand prior to use.

A sample of trimethylstannyl-MLA used for radio-iodination was purified by HPLC to eliminate any of iodo-MLA from the precursor, as the presence of unlabeled iodo-MLA would reduce the specific activity of the final radiolabeled product. HPLC analysis showed that the contamination of iodo-MLA in the trimethylstannyl-MLA precursor was less than 0.027%. Since the ratio of trimethylstannyl-MLA/$Na^{125}$I was 17, the effect on specific activity of the labeled product was less than 0.46% (0.027% 17), which was within normal experimental error. The radio-iodination (radio-iododestannylation) process of the precursor was completed within one minute at room temperature using chloramine-T as oxidant. The total radiochemical yield of [$^{125}$I]iodo-MLA after HPLC purification was 74%.

The pharmacological profile of [$^{125}$]iodo-MLA, based on the competition binding studies of compounds binding to the $\alpha4\beta2$, and non-competitive nAChRs, is consistent with this radioligand being specific for the $\alpha7$ nAChR subtype. Again, this is in agreement with the pharmacological profile of MLA (Alkondon et al, *Mol. Pharmacol.* 1992, 41, 802–808; Wonnacott et al, *Methods in Neurosciences* 1993; Vol. 12, pp 263–275) and [$^3$H]MLA (Davies et al, *Neuropharmacology* 1999, 38, 679–690).

The high specificity binding of the present ligands to $\alpha7$ nAChRs make it preferable to [$^{125}$I]$\alpha$-BGT in the study of this nAChR subtype. Moreover, its high specific activity makes it suitable for use in high throughput screening assays aimed at identifying nAChR subtype-specific ligands through competitions binding to determine candidates having higher specific affinity to the nAChRs. Since the addition of iodine-125 to MLA does not alter its specificity for the $\alpha7$ nAChR, an iodine-123 labeled MLA would be a useful ligand for imaging this nAChR subtype in vivo. Finding nAChR subtype specific ligands that are useful as an imaging agent is particularly relevant since reduced numbers of nAChRs have been observed in Parkinson's and Alzheimer's diseases and in schizophrenia (Brioni et al, *Adv. Pharmacol.* 1997, 37, 153–214).

Imaging techniques are well known in the art. Because radiolabeled iodo-MLA binds preferentially to $\alpha7$ nAChRs in vivo, it can be used as an imaging agent for both PET (Positron Emission Tomography) and SPECT scanning. PET scanning preferably uses the carbon-11 labeled form of the drug, while SPECT scanning preferably uses the I-123 labeled form of the drug. It can be used in the following ways.

A. To examine the density and distrubition of certain $\alpha7$ nAChRs in various parts of the body, including the brain.

B. To compare these densities in normal and disease states and use observed changes that can be associated with diseases as indicators diagnostic of disease states. The invention may also be employed to determine progression of the disease and/or prognosis as to various treatment regimens.

A brief description of an imaging procedure is as follows:

Tracer quantities (25–100 $\mu$g) of the radioactive iodine labeled ligand is injected intravenously into subjects positioned in a SPECT scanner. After injection of the compound, the scanner is turned on to begin to collect data. The ligand preferentially localizes to $\alpha7$ nAChRs over about one hour, with the best localization occurring at about 30–50 minutes. The amount of compound bound will reflect the density of $\alpha7$ nAChRs. The target of these experiments will be the hippocampus thalamus/hypothalamus where the $\alpha7$ nAChRs are concentrated. Disease states such as Parkinson's and Alzheimer's diseases will show a reduction in $\alpha7$ nAChRs density.

The present invention also provides an injectable composition suitable for use in imaging studies comprising a compound of Formula I where $R^1$ is a marker group detectable in vivo and a pharmacologically acceptable carrier. The injectable composition should contain an amount of ligand sufficient to administer up to 30 $\mu$g, preferably up to 25 $\mu$g, of ligand in a single injection. Suitable pharmacologically acceptable carriers include any conventional carriers used for injecting a patient particularly in imaging studies. Preferably the carrier is water.

The present invention also relates to a kit for imaging, comprising a compound of formula I where $R^1$ is a group that can be converted into the marker group detectable in vivo (such as trimethylstannyl), the reagents for performing the conversion into the marker group detectable in vivo (such as those shown in Scheme I for conversion of trimethylstannyl into the [$^{125}$I]-MLA compound) and a pharmacologically acceptable carrier.

Having generally described this invention, a further understanding can be obtained by reference to certain specific examples which are provided herein for purposes of illustration only and are not intended to be limiting unless otherwise specified.

EXAMPLES

5-Iodo-methyllycactonic Acid (7)

A suspension of (S)-methylsuccinic acid (0.95 g, 7.2 mmol) in acetic anhydride (10 mL) was heated at reflux overnight. After removal of excess acetic anhydride, the white residue was dried under reduced pressure. A solution of the (S)-methylsuccinic anhydride (4) obtained was dissolved in $CHCl_3$ (10 mL) and was added to a suspension of 5-iodoanthranilic acid (3, 1.29 g, 7.2 mmol) in 10 mL $CHCl_3$, and the mixture was heated on a steam bath for 30 min and evaporated to dryness. Flash chromatography using silica gel column and eluting with a solvent system of hexane:ethyl acetate:methanol:acetic acid (250:45:5:4) gave the succinimidic acids to (2.16 g, 80%) as a mixture of two isomers 5 and 6. $^1$H NMR ($CD_3OD$) δ1.26 (2 d, J=9.9 Hz), 2.52 (m, 1H), 2.80 (m, 2), 7.80 (1, aromatic), 8.34 (m, 2H).

A solution of the above succinimidic acid (3 g, 7.95 mmol) (obtained from two separate experiments) and triethylamine (4 g, 40 mmol) in 300 mL toluene was heated to reflux overnight. After removal of the solvent, the residue was chromatographed on silica gel, eluting with the same solvent system to give 1.72 g (60%) of 5-iodo-methyllycactonic acid (7). A sample recrystallized from ether/pet ether had mp 180–182° C.; $[a]^{25}_D$ –1.48° (c, 1.105, $CH_3OH$). Analysis calcd for $C_{12}H_{10}NO_4I$: C, 40.13; H, 2.81; N, 3.90; I, 35.34. Found: C, 40.16; H, 2.81; N, 3.83; I, 35.43.

Iodo-methyllycaconitine (Iodo-MLA)

To a stirred solution of the 5-iodo-methyllycaconitinic acid (7) (540 mg, 1.5 mmol) in dry pyridine (7 mL) was added p-toluenesulfonyl chloride (570 mg, 3 mmol). After cooling to 0° C., lycactonine (700 mg, 1.5 mmol)[1] was added, and the mixture was kept at 0–5° C. overnight. The mixture was diluted with water (50 mL) and extracted with chloroform (325 mL). The organic solution was washed with water and brine and was dried over $Na_2SO_4$. After removal of the solvents, the residue was purified by silica gel chromatography, eluting with a solvent system of $CHCl_3$:$CH_3OH$:$NH_4OH$ (200:9:1) to give 0.86 (71%) of pure iodo-methyllycaconitine. The citrate salt had mp 115–116° C.; $[a]^{25}_D$+25.5° C. (c, 0.255, $CH_3OH$). $^1$H NMR δ1.27 (t, 3H), 1.37 (d, 3), 2.47 (q, 2), 3.1 (s, 3H), 3.26 (s, 3H), 3.3 (s, 3H), 3.37 (s, 3H), 7.16 (d, 1H), 8.11 (d, 1H), 8.35 (s, 1H).

Analysis calcd for $C_{43}H_{57}N_2O_{17}I$: C, 51.60; H, 5.74; N, 2.80. Found: C, 51.42; H, 6.11; N, 3.22.

Trimethylstannylmethyllycaconitine (Trimethylstannyl-MLA)

A solution of iodo-methyllycaconitine (202 mg, 0.25 mol) and 20 mg of tetrakis(triphenylphosphine)palladium(0) and hexamethylditin (0.120 mL) in toluene (5 mL) under argon was gently refluxed overnight. The solvent was removed under reduced pressure, and the residue was chromatographed using silica gel, eluting with a solvent mixture of ether and triethylamine (9:1) to give 0.168 mg of product.

This product was further purified by silica gel chromatography using 5% methanol in chloroform as the eluent to give 0.148 g (70%) of pure trimethylstannyl methyllycaconitine as a white foamy solid. $^1$H NMR ($CDCl_3$) δ0.11 (s, 9H), 0.81 (t, 3H), 1.20 (d, 3H), 3.01 (s, 3H), 3.13 (s, 3H), 3.14 (s, 3H), 3.17 (s, 3H), 7.0 (d, 1H), 7.43 (d, 1H), and 7.92 (s, 1H).

Analysis calcd for $C_{40}H_{58}N_2O_{10}SnO0.5$ $H_2O$: C, 56.00; H, 6.84; N, 3.07. Found: C, 26.21; H, 6.96; N, 3.28.

[$^{125}$I]Iodo-methyllycaconitine ([$^{125}$I]Iodo-MLA)

To a solution of trimethylstannyl methyllycaconitine (MLA-tin) (0.25 mg, 0.30 μmol. purified by HPLC four times) in MeOH/HOAc (80 μL. 90/10 v/v) in a Reacti-Vial (1 mL) was added aqueous chloramine-T solution (20 μL, 10 mM, 0.2 μmol), followed by sodium iodide-125 (1875 Ci/mmol, 69.4 GBq/μmol, 21 mCi in NaOH solution, pH 9.0) which was centrifuged for 1 min at 600 rpm. The sodium iodide-125 vial was washed with MeOH/HOAc (20 μL, 90/10 v/v), and the washings were transferred back to the Reacti-vial. The vial was capped, and the solution in the vial was stirred vigorously for 1 min with a Vortexer. The reaction was then quenched by adding aqueous sodium metabisulfite ($Na_2S_2O_5$, 40 μL, 20 mM, 0.8 μmol) and stirring vigorously for 1 min with the Vortexer. The entire reaction mixture was loaded onto a Waters SymmetryShield RP8 column (3.9×150 mm, 5μ) preceded by a Waters Sentry Guard column (3.9×20 mm, 5μ). The column was eluted with 25% EtOH+75% [$H_2O$+citric acid (10 mM)+potassium citrate (9.9 mM), pH=4.33] at a flow rate of 1.0 mL/min. The eluent was collected as 1-mL fractions, and the fractions containing the most radioactivity (fraction 16) was diluted to 10 mL with the HPLC mobile phase. HPLC analysis of this fraction under the same conditions with a fresh column and a β-RAM radio-detector showed the labeled product in 98.7% purity ($t_R$=15.6 min, k=8.2). The radiochemical purity of the labeled product was also determined by TLC-radioscan by co-spotting with unlabeled authentic iodo-MLA and eluting with diethyl ether:dichloromethane:methanol:ammonium hydroxide=6:6:1:0.1; the purity of the product was 98.9% ($R_f$=0.34). The purified labeled compound was counted by a liquid scintillation analyzer (Packard 2200CA), indicating a 73.8% overall radiochemical yield.

Tissue Preparation

Frozen male rat cerebral cortex (Pel-Freez Biologicals, Rogers, Ak.) was homogenized (polytron) in 99 volumes of ice-cold 50-mM Tris buffer (assay buffer; pH 7.4 @ 4° C.) containing 120 mM NaCl, 5 mM KCl, 2 mM $CaCl_2$, and 1 mM $MgCl_2$. The homogenate was sedemented at 35,000×g for 10 min at 4° C. and the supernatant discarded. The pellet was washed twice more with the original volume of buffer. After the last sedimentation step, the pellet was resuspended in one-tenth the original volume of buuffer and stored at –80° C. until needed. On the day of assay, the tissue was thawed and diluted to a concentration of approximately 1 mg protein/mL for use in the binding assays.

[$^{125}$I]Iodo-MLA Binding Experiments

Saturation binding experiments were carried out in assay buffer for 2 h at 4° C. in a final volume of 0.5 mL. Binding assays were run in duplicate in 1.4 mL polypropylene tubes (Matrix to Technologies Corporation, Hudson, N.H.) in a 96-well array. Each sample contained approximately 200 ug of protein and various (8–12) concentrations of [$^{125}$I]iodo-MLA ranging from 0.02 to 22 nM. Nonspecific binding was determined for each concentration using 300 uM nicotine. The apparent rate of association ($K_{obs}$) and the rate of dissociation ($K_{off}$) were determined using similar assay conditions except that a single radioligand concentration of approximately 0.3 nM was used. For the association experiments, the radioligand was added to the tissue homogenate at various times ranging from 0.5 to 120 min. For the dissociation experiments, samples were allowed to reach equilibrium (2 h. incubation at room temperature) before being chilled on ice for 20 min. Dissociation of the radioligand was achieved by adding an ice-cold aliquot of 300 uM nicotine at different times (0.5 to 120 min). The competition binding assays were carried out in duplicate using 10–12 different concentrations of the test compounds. In a final volume of 0.5 mL each assay sample contained 200 ug protein, test compound and 100–150 pM [$^{125}$I]iodo-MLA. Samples were incubated for 2 h at room temperature, and nonspecific binding was determined in the presence of 300 uM nicotine. These experiments were run in both borosilicate glass test tubes and in 1.4 mL plastic tubes in a 96-well array. The competition binding studies run in 96-well format were pipetted using a MultiProbe II$_{EX}$ (Packard Instruments, Meriden, Conn.) robotic liquid handling system. The data from the 96-well and test tube assay were pooled since they yielded similar results.

For the brain region binding studies, adult male rats (N=2) were killed by decapitation and their brains rapidly removed, placed on a cold plate, and dissected into the cerebellum, hippocampus, thalamnus/hypothalamus, and striatum. The regions were frozen on dry ice and stored at −80° C. until use. Homogenate preparation and assay conditions were similar to those described above to the 96-well format competition binding assays except that total and nonspecific binding samples were run for each brain region homogenate. Homogenate protein content was determined using the BioRad D$_C$ protein assay kit.

A Multimate harvester (Packard; 96-well plates) or a Brandel 48-cell harvester (Brandel Scientific, Gaithersburg, Md.; test tubes) was used to separate bound radioligand from free by rapid vacuum filtration onto GF/B filters presoaked for at least 30 min in assay buffer containing 0.15% bovine serum albumin. The filters were washed with approximately 4 mL (96-well) or 6 mL (test tubes) of ice-cold 10-mM Tris buffer (pH 7.4 @ 4° C.; no salts) and dried prior to the addition scintillant: 35 uL of Microscint 20 (Packard) per well or 12 mL of Ultima Gold (Packard) per dram vial. The amount of radioligand remaining on each filter was determined using either a TopCount microplate scintillation counter (70% efficiency; Packard) or a TriCarb 2200 scintillation counter (70% efficiency; Packard).

Data Analysis

The binding data were analyzed using nonlinear regression (GraphPad Prism v. 3.0; GraphPad Software, San Diego, Calif.). The saturation, association, and dissociation binding data were fit to their respective one- or two-site models and the fits compared using an F test. The equation, (K$_{obs}$−K$_{on}$)/[L]), was used to calculate the K$_{on}$, where L equaled the assay concentration of the radioligand. The K$_d$ was determined from the saturation binding curves and also from the equation, K$_d$=K$_{off}$/K$_{on}$. The data from the competition binding studies were plotted as percent inhibition of binding vs. log concentration and fit to a sigmoid curve to calculate the IC$_{50}$. The Cheng-Prusoff equation$^{2\cdot}$ K$_I$=IC$_{50}$/(1+([L]/K$_d$)), was used to calculate the K$_i$ from the IC$_{50}$. The K$_d$ determined from saturation binding experiments was used for these calculations. The data are reported as the arithmetic mean±SEM.

Results of Binding Studies

The specificity of iodo-MLA for the α7 nAChR relative to α4β2 was assessed in 2–3 preliminary competition binding experiments using [$^{125}$I]α-BGT, [$^3$H]MLA, or [$^3$H]epibatidine (Table 1).

TABLE 1

K$_i$ Values of MLA and Iodo-MLA

| Compound | Binding Affinity (K$_i$ in nM) | | |
|---|---|---|---|
| | [$^{125}$I]α-BGT | [$^3$H]MLA | [$^3$H]Epibatidine |
| MLA | 0.8 ± 0.1 | 0.6 ± 0.02 | >1 μM |
| iodo-MLA | 1.3$^a$ | 1.6 ± 0.4 | >1 μM |

$^a$Represents a single determination.

MLA and iodo-MLA showed high affinity for the α7 nAChR while both exhibited poor affinity at α4β2 nAChRs. The results indicate that adding an iodine to the aromatic ring in MLA does not decrease its potency at the α7 nAChR and suggested that [$^{125}$I]iodo-MLA might be a useful radioligand for the α7 nAChR.

[$^{125}$I]Iodo-MLA binding was characterized in rat brain cerebral cortex homogenates. Specific binding of [$^{125}$I]iodo-MLA was typically 70–80% of total binding at 100 pM, and it was linear with protein concentration (up to 300 μg protein/assay tube; not shown). The data from the saturation binding experiments (N=6) revealed that the binding was saturatable and that the specific binding was best fit by a one-site model that gave an affinity constant (Kd) of 1.8±0.4 nM and a Bmax of 68±3 fmol/mg protein. Both values are in general agreement with corresponding values determined for [$^3$H]MLA (Davies et al, Neuropharmacology 1999, 38, 679–690). The specific binding data from the association binding experiments (N=3) were best fit by a one-phase exponential association equation with a K$_{obs}$=0.08±0.02 min$^{-1}$ and a t$_{1/2}$=10.5±3.1 min. The dissociation data determined from three experiments were best fit by a one-phase exponential decay equation which gave a K$_{off}$ of 0.07±0.01 min$^{-1}$ and a t$_{1/2}$=10.3±1.6 min. Based on these two rate constants, the K$_{on}$ was calculated to be 0.053 M$^{-1}$ min$^{-1}$, and the derived K$_d$ was equal to 2.1 nM.

The specificity of [$^{125}$I]iodo-MLA binding to the α7 nAChR first was investigated using ligands known to bind to nAChRs. Of the compounds tested, MLA and α-bungarotoxin displaced [$^{125}$I]iodo-MLA with a K$_i$ in the low nanomolar range. Nicotine, dihydro-b-erythroidine (an α4β2-selective nAChR antagonist), and the noncompetitive nAChR antagonist, mecamylamine, were all weak or ineffective at displacing [$^{125}$I]iodo-MLA (see Table 2).

TABLE 2

Inhibition of [$^{125}$I]Iodo-MLA Binding

| Compound | K$_{I\ (nM)}$ |
|---|---|
| Methylllycacotinine | 3.4 ± 0.7 |
| α-Bungarotoxin | 2.0 ± 0.1 |
| 3-Cinnamylidene-anabasine | 15.3 ± 2.0 |
| (−)-Nicotine | 675 ± 33 |
| Dihydro-β-erythroidine | >10,000 |
| Mecamylamine | >10,000 |

We also determined [$^{125}$I]iodo-MLA binding in rat brain regions known to contain high (hippocampus and thalamus/hypothalmus) and low (cerebellum and striatum) levels of α7 nAChRs based on [$^{125}$I]α-bungarotoxin binding (Marks et al, Mol. Pharmacol. 1986, 30, 427–436). For each region, the ratio of specific binding (fmou/mg protein) to specific cerebellar binding (control region) was calculated. The ratios were highest in the hippocampus (8.2±0.9; N=2;

mean±SD) and thalamus/hypothalamus (4.2±1.4), whereas the striatal [$^{125}$I]iodo-MLA binding ratio was not increased over the control (1.1±0.8). The regionally-selective increases in [$^{125}$I]iodo-MLA binding pattern were consistent with the ligand being selective for α7 nAChRs.

Obviously, numerous modifications and variations of the present invention are possible in light of the above teachings. It is therefore to be understood that, within the scope of the appended claims, the invention may be practiced otherwise than as specifically described herein.

We claim:

1. A compound of formula I:

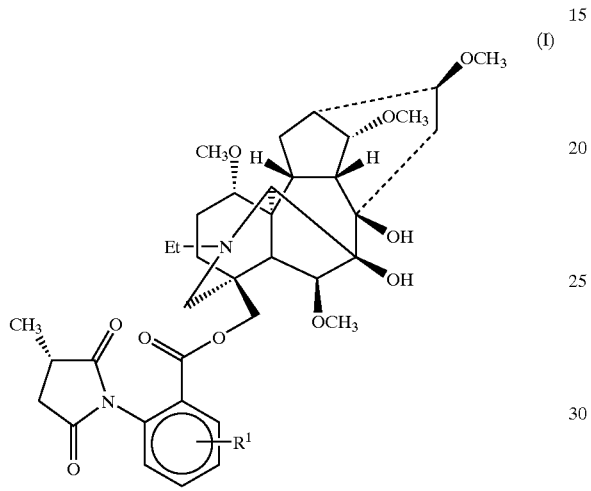

where $R^1$ is (i) a radioisotope selected from the group consisting of $^{125}$I, $^{123}$I, $^{124}$I, $^{120}$I, $^{11}$C and $^{18}$F, or (ii) a group selected from trihydrocarbylstannyl and trihydrocarbylsilyl.

2. The compound of claim 1, wherein $R^1$ is a radioisotope selected from the group consisting of $^{125}$I, $^{123}$I, $^{124}$I, $^{120}$I, $^{11}$C and $^{18}$F.

3. The compound of claim 1, having the formula

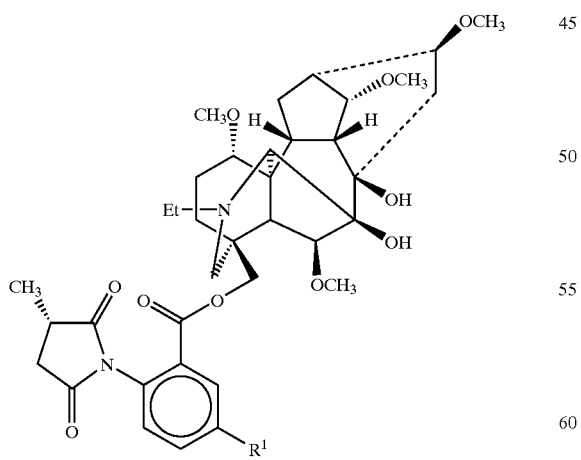

where $R^1$ is (i) a radioisotope selected from the group consisting of $^{125}$I, $^{123}$I, $^{124}$I, $^{120}$I, $^{18}$C and $^{18}$F or (ii) a group selected from the group consisting of trihydrocarbylsilyl and trihydrocarbylstannyl.

4. The compound of claim 1, wherein $R^1$ is a group selected from the group consisting of trihydrocarbylsilyl and trihydrocarbylstannyl.

5. The compound of claim 4, wherein $R^1$ is a group selected from the group consisting of trimethylsilyl and trimethylstannyl.

6. The compound of claim 5, wherein $R^1$ is trimethylstannyl.

7. An imaging method, comprising:

administering to a subject an effective imaging amount of a ligand, wherein the ligand is a compound of formula I:

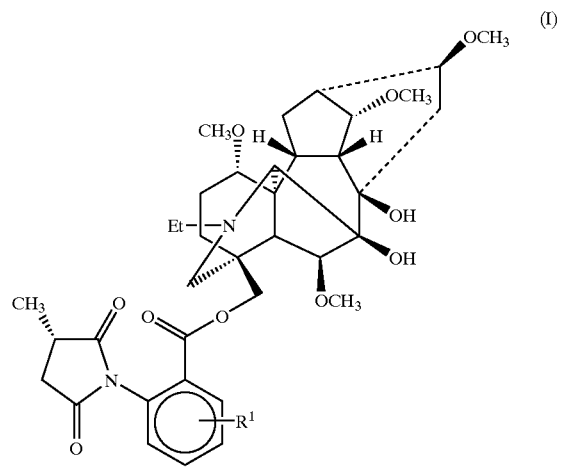

where $R^1$ is a radioisotope selected from the group consisting of $^{125}$I, $^{123}$I, $^{124}$I, $^{120}$I, $^{11}$C and $^{18}$F; and collecting imaging data from said subject using an imaging scanner for a period of time sufficient for said ligand to localize to α7 nAChRs.

8. The method of claim 7, wherein said ligand has the formula:

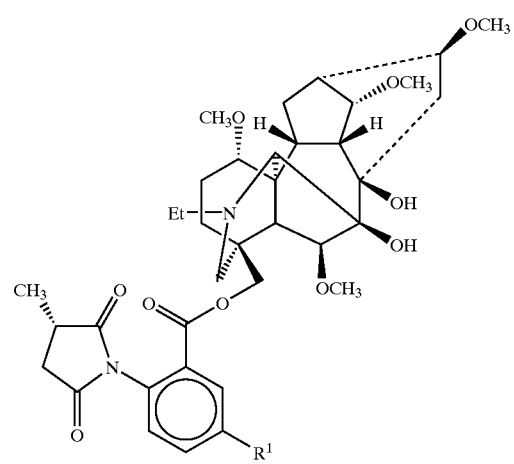

where $R^1$ is a radioisotope selected from the group consisting of $^{125}$I, $^{123}$I, $^{124}$I, $^{120}$I, $^{11}$C and $^{18}$F.

9. An injectable composition comprising a compound of formula I:

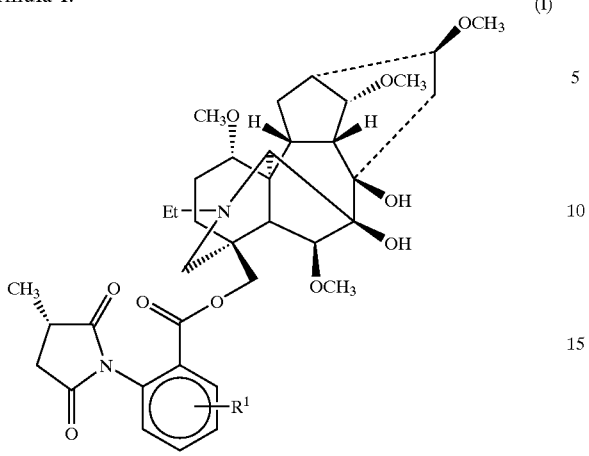

where $R^1$ is a radioisotope selected from the group consisting of $^{125}I$, $^{123}I$, $^{124}I$, $^{120}I$, $^{11}C$ and $^{18}F$; and a pharmacologically acceptable carrier.

10. The injectable composition of claim 9, wherein said compound has the formula:

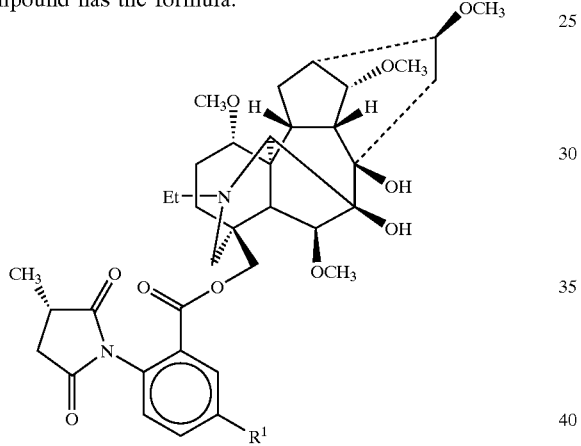

where $R^1$ is a radioisotope selected from the group consisting of $^{125}I$, $^{123}I$, $^{124}I$, $^{120}I$, $^{11}C$ and $^{18}F$.

11. A kit for imaging studies, comprising:

a compound of formula I:

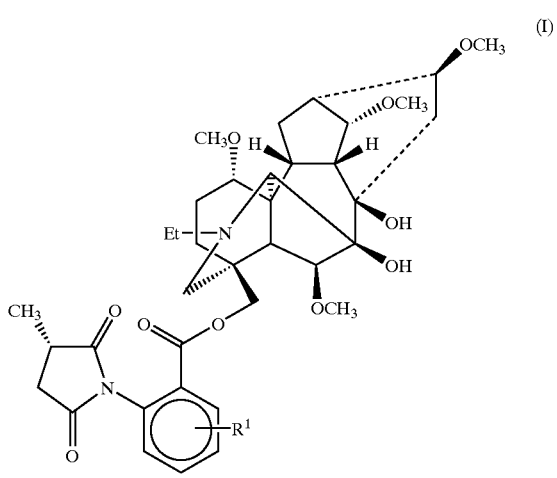

where $R^1$ is a group selected from the group consisting of trihydrocarbylsilyl and trihydrocarbylstannyl;

reagents to convert $R^1$ into a radioisotope selected from the group consisting of $^{125}I$, $^{123}I$, $^{124}I$, $^{120}I$, $^{11}C$ and $^{18}F$; and a pharmacologically acceptable carrier in which said $R^1$ group can be converted into the radioisotope and then injected into a subject to be imaged.

12. The kit of claim 11, wherein $R^1$ is trimethylstannyl.

13. The kit of claim 12 wherein said reagents to convert $R^1$ into the marker group detectable in vivo comprise (i) a radioisotope compound selected from $Na^{123}I$, $Na^{124}I$, $Na^{120}I$, and $Na^{125}I$; (ii) chloramine T and (iii) $Na_2S_2O_5$.

* * * * *

UNITED STATES PATENT AND TRADEMARK OFFICE
CERTIFICATE OF CORRECTION

PATENT NO. : 6,416,735 B1
DATED : July 9, 2002
INVENTOR(S) : F. Ivy Carroll et al.

It is certified that error appears in the above-identified patent and that said Letters Patent is hereby corrected as shown below:

Title page,
Item [54], "METHYLLCACONITINE" should read -- METHYLLYCACONITINE --.

Column 1,
Line 50, "cither" should read -- either --.
Line 50, "nicotinc" should read -- nicotine --.

Column 9,
Line 51, "prefereably" should read -- preferably --.

Column 10,
Line 6, "[$^{125}$]" should read -- [I$^{125}$] --.
Line 37, "distrubition" should read -- distribution --.

Column 11,
Line 40, "MLΛ" should read -- MLA --.

Column 13,
Line 25, "thalamnus" should read -- thalamus --.
Line 3, "addition scintillant" should read -- addition of scintillant --.
Line 59, "2." should read -- 2, --.

Column 14,
Line 53, "Methylllycacotinine" should read -- Methyllycaconitine --.
Line 60, "[$^{12}$5I]" should read -- [$^{125}$I] --.
Line 62, "hypothalmus" should read -- hypothalamus --.
Line 65, "fmon" should read -- fmol --.

Column 15,
Line 65, "$^{18}$C" should read -- $^{11}$C --.

UNITED STATES PATENT AND TRADEMARK OFFICE
CERTIFICATE OF CORRECTION

PATENT NO. : 6,416,735 B1
DATED : July 9, 2002
INVENTOR(S) : F. Ivy Carroll et al.

It is certified that error appears in the above-identified patent and that said Letters Patent is hereby corrected as shown below:

Column 18,
Line 38, "12 wherein" should read -- 12, wherein --.

Signed and Sealed this

Eighteenth Day of March, 2003

JAMES E. ROGAN
*Director of the United States Patent and Trademark Office*